United States Patent
Hua et al.

(10) Patent No.: US 11,786,674 B2
(45) Date of Patent: Oct. 17, 2023

(54) HIGH-FREQUENCY ULTRASONIC ATOMIZER STRUCTURE

(71) Applicant: FEELLIFE HEALTH INC., Guangdong (CN)

(72) Inventors: Jian Hua, Guangdong (CN); Xuefeng Song, Guangdong (CN)

(73) Assignee: FEELLIFE HEALTH INC., Shenzhen (CN)

( * ) Notice: Subject to any disclaimer, the term of this patent is extended or adjusted under 35 U.S.C. 154(b) by 656 days.

(21) Appl. No.: 15/733,529

(22) PCT Filed: Nov. 20, 2018

(86) PCT No.: PCT/CN2018/116505
§ 371 (c)(1),
(2) Date: Aug. 21, 2020

(87) PCT Pub. No.: WO2020/048008
PCT Pub. Date: Mar. 12, 2020

(65) Prior Publication Data
US 2021/0077751 A1    Mar. 18, 2021

(30) Foreign Application Priority Data

Sep. 6, 2018 (CN) .......................... 201811037741.1
Sep. 6, 2018 (CN) .......................... 201821457663.6

(51) Int. Cl.
*A61M 15/06* (2006.01)
*A24F 40/10* (2020.01)
(Continued)

(52) U.S. Cl.
CPC ........ *A61M 11/005* (2013.01); *A61M 15/001* (2014.02); *A61M 15/06* (2013.01);
(Continued)

(58) Field of Classification Search
CPC .......... A24F 40/05; A24F 40/20; A24F 40/00; A24F 40/10; A24F 7/02; B05B 17/0653;
(Continued)

(56) References Cited

U.S. PATENT DOCUMENTS

2017/0181470 A1* 6/2017 Li .......................... A24F 40/485
2018/0153217 A1* 6/2018 Liu ........................ A61M 15/06
2018/0317551 A1* 11/2018 Daryani .................. A24F 40/48

FOREIGN PATENT DOCUMENTS

CN          205337613 U       6/2016
CN          205567818 U       9/2016
(Continued)

OTHER PUBLICATIONS

ISA/CN, PCT International Search Report and Written Opinion dated May 29, 2019 issued in PCT International Application No. PCT/CN2018/116505.

*Primary Examiner* — Christopher R Dandridge
(74) *Attorney, Agent, or Firm* — Gottlieb, Rackman & Reisman, P.C.

(57) ABSTRACT

Provided is a high-frequency ultrasonic atomizer structure, comprising a main machine and a master frequency ultrasonic atomizer connected to the main machine. The master frequency ultrasonic atomizer comprises an outer sleeve, an upper cover and a base that are respectively and detachably connected at upper and lower ends of the outer sleeve, an inner tube support body and an ultrasonic atomization unit that are successively arranged inside the outer sleeve, and a liquid storage chamber formed between the inner tube support body and an inner wall of the outer sleeve. The upper cover and the inner tube support body form an air flow chamber therebetween. The master frequency ultrasonic atomizer further comprises a suction tube in communication with the interior of the air flow chamber arranged on the (Continued)

upper cover, and a plurality of air inlet holes in communication with the interior of the air flow chamber.

10 Claims, 3 Drawing Sheets

(51) Int. Cl.
    *B05B 17/06*     (2006.01)
    *A61M 11/00*     (2006.01)
    *A61M 15/00*     (2006.01)
    *A61M 5/00*     (2006.01)

(52) U.S. Cl.
    CPC ...... *A24F 40/10* (2020.01); *A61M 2205/8206* (2013.01); *B05B 17/0653* (2013.01)

(58) Field of Classification Search
    CPC ........ A61M 2205/8206; A61M 15/001; A61M 15/06; A16M 11/005
    See application file for complete search history.

(56) References Cited

FOREIGN PATENT DOCUMENTS

| | | |
|---|---|---|
| CN | 205728076 U | 11/2016 |
| CN | 206687171 U | 12/2017 |
| CN | 108355209 U | 8/2018 |
| KR | 20140002774 U | 5/2014 |

\* cited by examiner

HIGH-FREQUENCY ULTRASONIC ATOMIZER STRUCTURE

CROSS-REFERENCE TO RELATED APPLICATIONS

This application is filed on the basis of Chinese patent application No. 201811037741.1 filed Sep. 6, 2018, Chinese patent application No. 201821457663.6 filed Sep. 6, 2018, and PCT application PCT/CN2018/116505 filed Nov. 20, 2018, and claims priority of the patent applications, the entire contents of which are incorporated herein by reference.

TECHNICAL FIELD

The disclosure relates to the field of atomizers, and particularly to a high-frequency ultrasonic atomizer structure.

BACKGROUND

E-cigarettes, as an important application of atomizers, are a kind of products used for converting cigarette oil containing nicotine and other components into mist for inhalation by users. Such application replaces the traditional use of tobacco, gradually reducing the dependency of smokers on tobacco-based cigarettes, eventually to achieve the purpose of quitting smoking. Compared with the traditional tobacco, an E-cigarette has the advantages that: firstly, the E-cigarette does not produce open flame and thus is safer to use, thereby avoiding fire hazards; secondly, the E-cigarette does not burn, nor produce ash and cigarette butt, thus is more environmentally friendly; and thirdly, the E-cigarette does not produce second-hand smoke, and thus will not harm the surrounding people. At present, the E-cigarettes in the market are usually in the form of a combination of heating and ultrasonic atomization, that is, before ultrasonic atomized, the liquid is heated to a near atomization state by a heating wire, to be more easily dispersed into atomization particles by an ultrasonic atomization piece. Usually, the heating wire is at a very high temperature, as the atomizer is usually small in size and compact in internal structure, it is difficult to dissipate the heat generated by the heating wire, which inevitably causes the machine body to be hot, causing potential harm to the users. Moreover, an existing ultrasonic atomization piece is usually formed by firmly securing a metal substrate and a piezoelectric ceramic piece into one piece through a welding agent or adhesive, such that its production is relatively difficult, and the metal substrate is easy to be perforated if used carelessly. Besides, once the metal substrate is perforated, the whole ultrasonic atomization piece is difficult to be recycled, causing low yield and waste of materials in ultrasonic atomization production. In addition, the existing E-cigarette atomizers usually adopt a structure of combining the heating wire and oil guide cotton as an atomization core, and the oil guide cotton is easy to burn and age after being used for a period of time, which makes the atomization core difficult to clean.

SUMMARY

In view of the above problems, an object of the present invention is to provide a high-frequency ultrasonic atomizer structure with excellent heat dissipation and atomization, convenience in processing and lower cost in material.

In order to achieve the above object, the present invention provides a high-frequency ultrasonic atomizer structure comprising a main machine and a master frequency ultrasonic atomizer connected to the main machine. The master frequency ultrasonic atomizer comprises an outer sleeve, an upper cove and a base that are respectively and detachably connected at upper and lower ends of the outer sleeve, an inner tube support body and an ultrasonic atomization unit that are successively arranged inside the outer sleeve, a liquid storage chamber formed between the inner tube support body and an inner wall of the outer sleeve, an air flow chamber formed between the interior of the upper cover and the inner tube support body, a suction tube in communication with the interior of the air flow chamber arranged on the upper cover, and a plurality of air inlet holes in communication with the interior of the air flow chamber arranged in a side face of the upper cover. The inner tube support body comprises a disc and a vent tube, wherein the disc is arranged in the outer sleeve, connected to the upper cover and the outer sleeve respectively and provided with an inner chamber, and the vent tube which is arranged in the center of the disc and is in communication with the ultrasonic atomization unit. The inner chamber of the disc is in communication with the air flow chamber, and the vent tube is in communication with the inner chamber of the disc. The liquid storage chamber is an annular space defined by the disc, an outer side of the vent tube and an inner side of the outer sleeve, and the disc is provided with an oil injection hole in communication with the liquid storage chamber. The ultrasonic atomization unit comprises a first fixed seat arranged at an end of the vent tube and connected to the vent tube, a metal substrate arranged on the first fixed seat, a second fixed seat arranged on the base and spaced apart from the first fixed seat by a certain distance, a piezoelectric ceramic piece arranged on the second fixed seat, a spring arranged between the metal substrate and the piezoelectric ceramic piece and coming into contact with the metal substrate and the piezoelectric ceramic piece, respectively, and an atomization liquid chamber formed among the first fixed seat, the second fixed seat and the inner side of the outer sleeve. The first fixed seat is provided with liquid guide holes for guiding the liquid in the liquid storage chamber into the atomization liquid chamber, and the spring is immersed by the liquid in the atomization liquid chamber. The base is provided with a first connecting tube which extends outwards and has external threads, and a first electrode connected to the piezoelectric ceramic piece is arranged in the first connecting tube. The metal substrate is provided with a micropore area corresponding in position to an orifice of the vent tube. The orifice of the vent tube is spaced away from the micropore area by a certain distance, and the metal substrate may be a stainless-steel sheet. A suction nozzle is sleeved on the suction tube. The liquid guide holes are provided in two and are symmetrically arranged at an edge of the first fixed seat. In addition, the air inlet holes, the vent tube and the suction tube are in communication with one another.

In some embodiments, the outer sleeve, the inner tube support body and the ultrasonic atomization unit are detachably connected.

In some embodiments, the first fixed seat and the second fixed seat are respectively provided with annular recesses for fixing the metal substrate and the piezoelectric ceramic piece. In addition, the first fixed seat and the second fixed seat are respectively provided at opposite centers thereof with a recessed area which can limit the spring 605 and prevent the spring 605 from deviating.

In some embodiments, the first fixed seat and the second fixed seat are made of silica gel material.

In some embodiments, the outer sleeve is made of transparent material, to facilitate observation of the liquid level in the sleeve.

In some embodiments, a sealing ring is arranged between the first electrode and the first connecting tube.

In some embodiments, the metal substrate is made of a steel sheet with a thickness of 0.05-0.5 mm, on which 1500-10000 micropores with diameters ranging from 2 to 5 microns are distributed in the micropore area.

In some embodiments, the main machine comprises a housing, a key disposed on a surface of the housing, a battery arranged in the housing, a circuit board arranged at a position corresponding to the position of the key on the housing and connected to the battery, a second connecting tube arranged at an end of the housing, and a second electrode arranged in the second connecting tube and connected to the battery, wherein the second connecting tube is provided with internal threads corresponding to the external threads on the first connecting tube, through which the first and second connecting tubes are connected. The first electrode is connected to the second electrode.

In some embodiments, the circuit board comprises a main control unit, an atomization piece driving unit connected to the main control unit, a key unit connected to the main control unit, a boosting unit connected to the atomization piece driving unit, and a second motor connected to the atomization piece driving unit. The boosting unit is connected to the battery.

In some embodiments, the atomization piece driving unit is powered through the second electrode, the first electrode and the piezoelectric ceramic piece in sequence.

The high-frequency ultrasonic atomizer structure of the invention has the advantages of good heat dissipation, excellent atomization effect, easy production and lower material cost, in detail: (1) as the liquid is subjected to atomization and is pre-processed in a non-heating process, the overheating problem of the machine body is solved, and a good overall heat dissipation is achieved. (2) The metal substrate and the piezoelectric ceramic piece are separately arranged, a spring is arranged between and abutting the metal substrate and the piezoelectric ceramic piece. When the piezoelectric ceramic piece is driven by voltage to vibrate mechanically at a certain frequency, the spring is forced to vibrate, and the spring and the piezoelectric ceramic piece vibrate mechanically at the same frequency after reaching stabilization, thus driving the metal substrate to oscillate at a high speed, and enabling the liquid medicine to be quickly ejected through the micropore area on the metal substrate. At this time, before the liquid is ejected by the metal substrate, the liquid may immerse the spring and be mechanically oscillated by the spring. The liquid molecules around the spring coil may accelerate irregular motion due to the high-frequency vibration of the spring, which increases the activity of the liquid molecules and makes the liquid easier to break up into small molecular particles, i.e. atomization, which is especially effective for relatively viscous liquid. The spring not only plays a role of driving, but also plays a role like stirring. Therefore, compared with the existing atomization structure, the improved master frequency ultrasonic atomizer directly atomizes static liquid, which makes the atomization effect more notable, especially for slightly viscous liquid, such as cigarette oil. Therefore, the purpose of providing notable atomization effect is achieved. (3) according to the invention, a split structure of the metal substrate and the piezoelectric ceramic piece is adopted, welding and bonding are no longer require, processing steps are reduced, it is beneficial to the recycle and reuse of the metal substrate and the piezoelectric ceramic piece. (4) In the present invention, the ultrasonic atomizer is used to atomize at normal temperature by mechanical vibration, and the ultrasonic atomizer is detachable, making cleaning more convenient.

DETAILED DESCRIPTION

The present invention will be further explained below in detail by embodiments with reference to the accompanying drawings.

Figure 1:
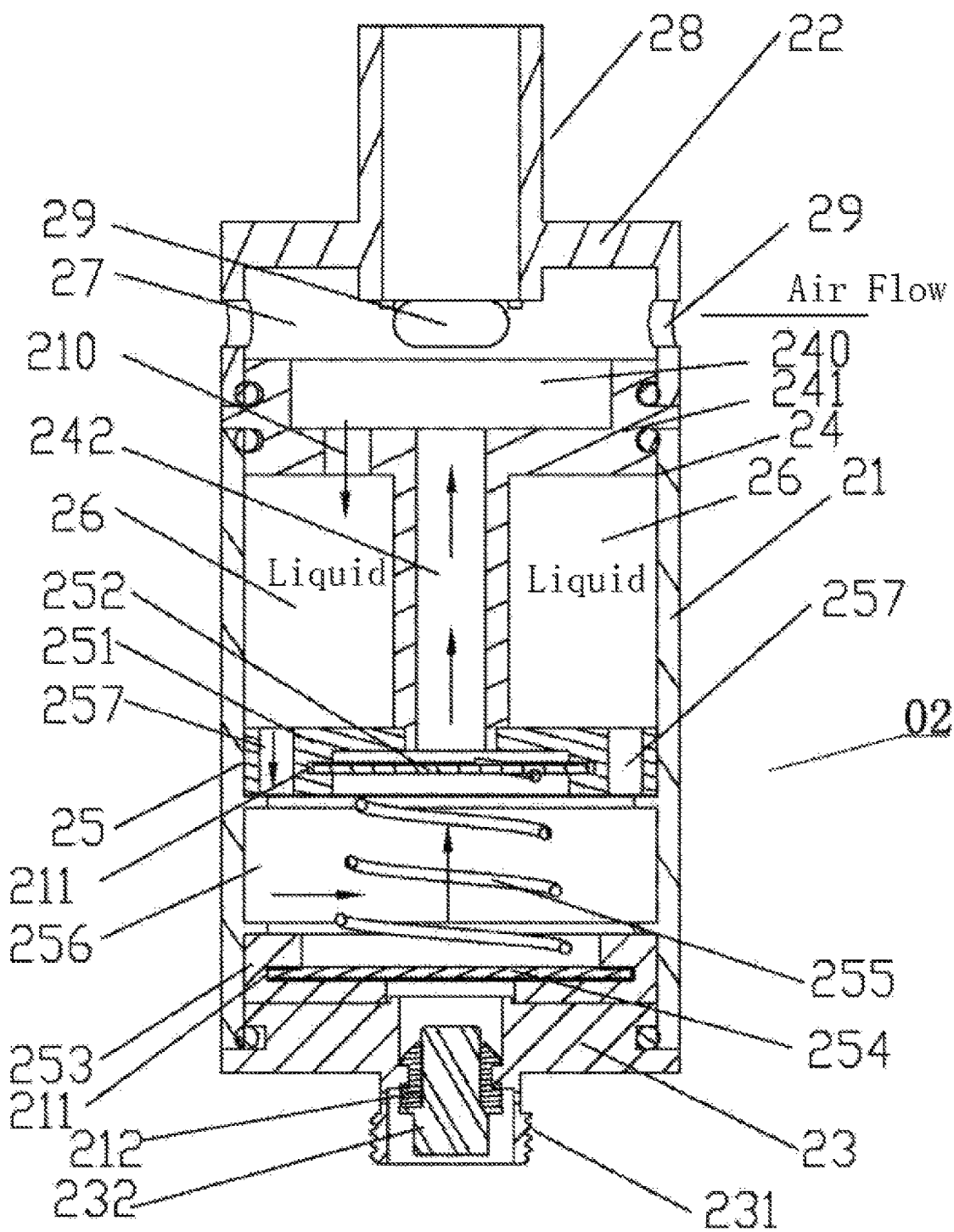
FIG. 1 is a schematic diagram of an internal structure of a master frequency ultrasonic atomizer of the present invention.

As shown in FIG. 1, a high-frequency ultrasonic atomizer structure comprises a main machine 01 and a master frequency ultrasonic atomizer 02 connected to the main machine 01. The master frequency ultrasonic atomizer 02 comprises an outer sleeve 21, an upper cover 22 and a base 23 that are respectively and detachably connected at upper and lower ends of the outer sleeve 21, an inner tube support body 24 and an ultrasonic atomization unit 25 that are successively arranged inside the outer sleeve 21, and a liquid storage chamber 26 formed between the inner tube support body 24 and an inner wall of the outer sleeve 21. The master frequency ultrasonic atomizer 02 further comprises an air flow chamber 27 formed between the interior of the upper cover 22 and the inner tube support body 24, a suction tube 28 in communication with the interior of the air flow chamber 27 arranged on the upper cover 22, and a plurality of air inlet holes 29 in communication with the interior of the air flow chamber 27 arranged in a side face of the upper cover 22. The inner tube support body 24 comprises a disc 241 and a vent tube 242, wherein the disc 241 is arranged in the outer sleeve 21, connected to the upper cover 22 and the outer sleeve 21 respectively and provided with an inner chamber 240, and the vent tube 242 is arranged in the center of the disc 241 and is in communication with the ultrasonic atomization unit 25. The disc 241 has an inner chamber 240 in communication with the air flow chamber 27 and the vent tube 242. The liquid storage chamber 26 is an annular space defined by the disc 241, an outer side of the vent tube 242 and an inner side of the outer sleeve 21, and the disc 241 is provided with an oil injection hole 210 in communication with the liquid storage chamber 26. The ultrasonic atomization unit 25 comprises a first fixed seat 251 arranged at an end of the vent tube 242 and connected to the vent tube 242, a metal substrate 252 arranged on the first fixed seat 251, a second fixed seat 253 arranged on the base 23 and spaced apart from the first fixed seat 251 by a certain distance, a piezoelectric ceramic piece 254 arranged on the second fixed seat 253, a spring 255 arranged between the metal substrate 252 and the piezoelectric ceramic piece 254 and coming into contact with the metal substrate 252 and the piezoelectric ceramic piece 254 respectively, and an atomization liquid chamber 256 formed among the first fixed seat 251, the second fixed seat 253 and the inner side of the outer sleeve 21. The first fixed seat 251 is provided with liquid guide holes 257 for guiding liquid in the liquid storage chamber 26 into the atomization liquid chamber 256, such that the spring 255 is immersed by the liquid in the atomization liquid chamber 256. The base 23 is provided with a first connecting tube 231 which extends outwards and has external threads, and a first electrode 232 arranged in the first connecting tube 231 and connected to the piezoelectric ceramic piece 254. The metal substrate 252 is provided with a micropore area corresponding to an orifice of the vent tube 242 in position. The orifice of the vent tube is spaced away from the micropore area by a certain distance, and the metal substrate 252 may be a stainless-steel sheet. The suction tube 28 may be provided with a suction nozzle sleeved thereon. The liquid guide holes 257 are provided in two and are symmetrically arranged at an edge of the first fixed seat 251. In addition, the air inlet holes 29, the vent tube 242 and the suction tube 28 are in communication with one another. The outer sleeve 21, the inner tube support body 24 and the ultrasonic atomization unit 25 are detachably connected. The first fixed seat 251 and the second fixed seat 253 are respectively provided with annular recesses 211 for fixing the metal substrate 252 and the piezoelectric ceramic piece 254. In addition, the first fixed seat 251 and the second fixed seat 253 are respectively provided at opposite centers thereof with a recessed area for limiting and preventing the spring 255 from deviating. The first fixed seat 251 and the second fixed seat 253 may be made of silica gel material. The outer sleeve 21 may be made of transparent material, for facilitating the observation of the liquid level in the sleeve. The outer sleeve 21 comprises a sealing ring 212 arranged between the first electrode 232 and the first connecting tube 231. The metal substrate 252 is made of a steel sheet with a thickness of 0.05-0.5 mm, on which 1500-10000 micropores with diameters ranging from 2 to 5 microns are distributed in the micropore area.

When the piezoelectric ceramic piece is powered on and driven at a certain frequency, the piezoelectric ceramic piece and the spring 255 resonate and oscillate, driving the metal substrate 252 to oscillate at a high speed, such that the liquid medicine can be quickly ejected through the micropore area in the metal substrate 252. Before the liquid is ejected by the metal substrate 252, the liquid may immerse the spring 255 and will be dispersed by the mechanical oscillation of the spring 255. The misty particles sprayed from the metal substrate 252 pass through the vent tube 242, and are sucked into the human body through the suction tube 28 together with the air flow entering from the air inlet holes 29. The ultrasonic atomizer structure and atomization method thereof may be applied to medical treatment and electronic cigarette applications.

Figure 2:
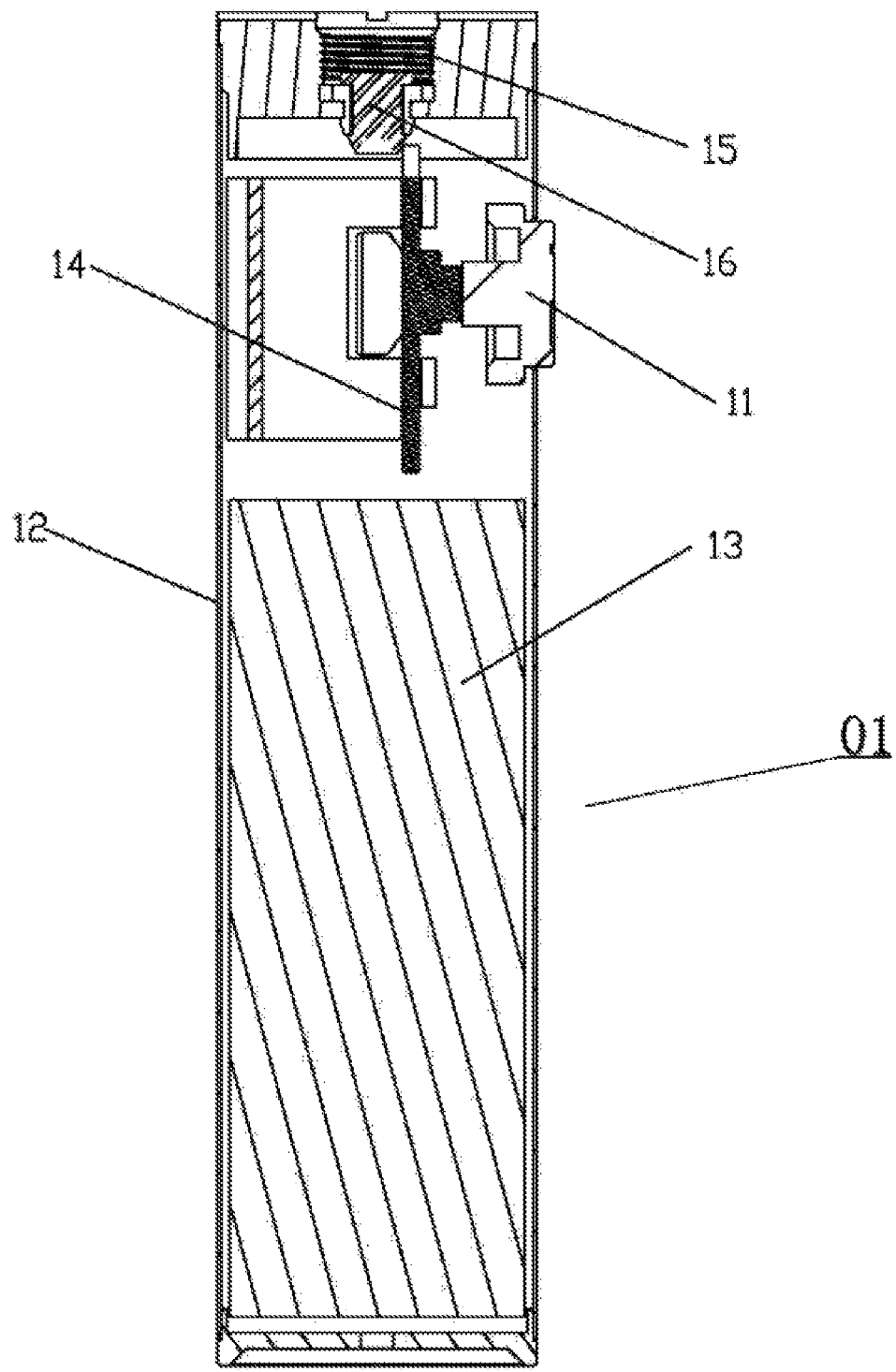
FIG. 2 is a schematic diagram of the internal structure of the main machine of the present invention.
Figure 3:
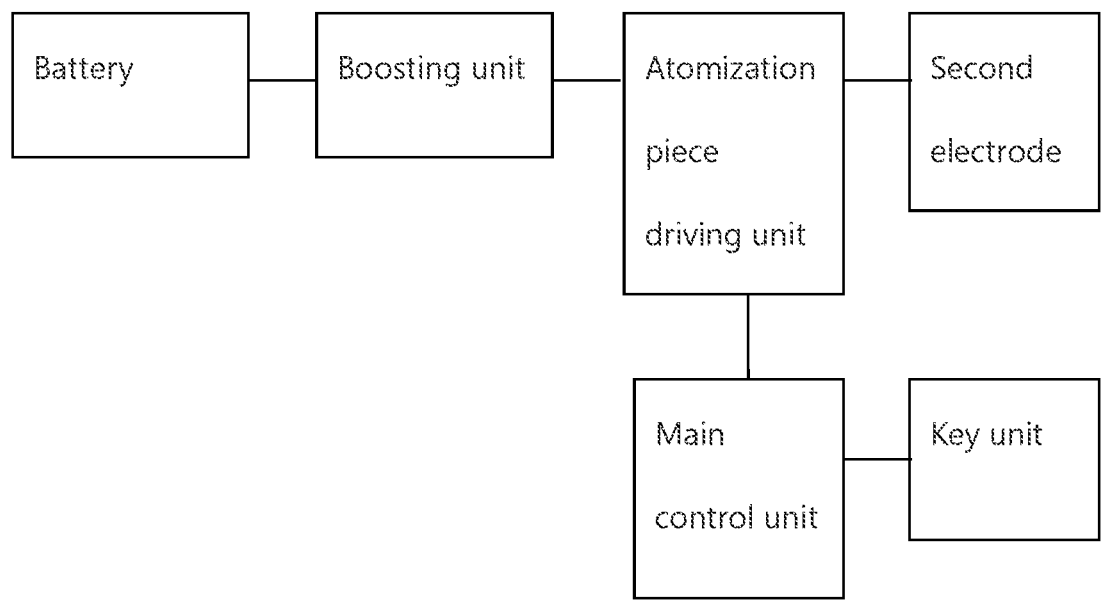
FIG. 3 is a block diagram of a circuit board of the present invention.

As shown in FIGS. 2-3, the main machine 01 comprises a housing 12, a key 11 arranged on a surface of the housing 12, a battery 13 arranged in the housing 12, a circuit board 14 arranged in a position corresponding to where the key 11 is arranged on the housing 12 and connected to the battery 13, a second connecting tube 15 arranged at an end of the housing 12, and a second electrode 16 arranged in the second connecting tube 15 and connected to the battery, wherein the second connecting tube 15 is provided with internal threads corresponding to the external threads of first connecting tube 231, the second connecting tube 15 and the first connecting tube 231 are connected by the threads. The first electrode 232 is connected to the second electrode 16. The circuit board 14 comprises a main control unit, an atomization piece driving unit connected to the main control unit, and a key unit connected to the main control unit, a boosting unit connected to the atomization piece driving unit and a second motor connected to the atomization piece driving unit. The boosting unit is connected to the battery 13. The main control unit is used as a logic control part of the whole circuit, and is configured to output driving frequency and recording information. The voltage boosting unit is used for outputting a voltage applied on the atomization piece driving unit. The atomization piece driving unit is used for driving the piezoelectric ceramic piece 254 according to the driving frequency and the driving voltage, and the key unit is used for interactively inputting signals to start the program burned in the main control unit. The atomization piece driving unit is electrically connected through the second electrode 16, the first electrode 232 and the piezoelectric ceramic piece 254 in sequence.

The embodiments described above are only some embodiments of the present invention. On the premise of not departing from the concept of the present invention, for those ordinary skilled in the art, many modifications and improvements may be made, and these modification and improvements should also be deemed to be fallen into the protection scope of the present invention.

What is claimed is:

1. A high-frequency ultrasonic atomizer structure, comprising:
   a main machine; and
   a master frequency ultrasonic atomizer connected to the main machine, the master frequency ultrasonic atomizer comprising:
   an outer sleeve, having a upper end and a lower end,
   an upper cover,
   a base, comprising:
   a first connecting tube, extending outwards and provided with external threads, and
   a first electrode, arranged in the first connecting tube,
   wherein the upper cover and the base are detachably connected at the upper end and the lower end of the outer sleeve, respectively;
   an inner tube support body,
   an ultrasonic atomization unit,
   wherein the inner tube support body and the ultrasonic atomization unit are successively arranged inside the outer sleeve;
   a liquid storage chamber, formed between the inner tube support body and an inner wall of the outer sleeve;
   an air flow chamber, formed between the interior of the upper cover and the inner tube support body;
   a suction tube, arranged on the upper cover and in communication with the interior of the air flow chamber;
   a plurality of air inlet holes, arranged in a side face of the upper cover and in communication with the interior of the air flow chamber;
   wherein, the inner tube support body comprises:
   a disc, arranged in the outer sleeve, connected to the upper cover and the outer sleeve, respectively, and provided with an inner chamber in communication with the air flow chamber and an oil injection hole in communication with the liquid storage chamber, and
   a vent tube, having an orifice, arranged in a center of the disc and in communication with the ultrasonic atomization unit and the inner chamber of the disc;
   wherein, the liquid storage chamber is an annular space defined by the disc, an outer side of the vent tube and an inner side of the outer sleeve together;
   wherein, the ultrasonic atomization unit comprises:
   a first fixed seat arranged at an end of the vent tube and connected to the vent tube, a metal substrate arranged in the first fixed seat, and provided with a micropore area corresponding to the orifice of the vent tube in position, a second fixed seat arranged on the base and spaced apart from the first fixed seat by a certain distance, a piezoelectric ceramic piece arranged on the second fixed seat and connected to the first electrode, a spring, arranged between the metal substrate and the piezoelectric ceramic piece, and in contact with the metal substrate and the piezoelectric ceramic piece, respectively, and an atomization liquid chamber formed among the first fixed seat, the second fixed seat and the inner side of the outer sleeve;

wherein, the first fixed seat is provided with liquid guide holes for guiding liquid in the liquid storage chamber into the atomization liquid chamber, and the spring is immersed by the liquid in the atomization liquid chamber.

2. The high-frequency ultrasonic atomizer structure of claim 1, wherein the outer sleeve, the inner tube support body and the ultrasonic atomization unit are detachably connected.

3. The high-frequency ultrasonic atomizer structure of claim 1, wherein the first fixed seat and the second fixed seat are respectively provided with annular recesses for fixing the metal substrate and the piezoelectric ceramic piece.

4. The high-frequency ultrasonic atomizer structure of claim 1, wherein the first fixed seat and the second fixed seat are made of silica gel material.

5. The high-frequency ultrasonic atomizer structure of claim 1, wherein the outer sleeve is made of transparent material, for facilitating observation on the liquid level in the sleeve.

6. The high-frequency ultrasonic atomizer structure of claim 1, further comprising a sealing ring arranged between the first electrode and the first connecting tube.

7. The high-frequency ultrasonic atomizer structure of claim 1, wherein the metal substrate is made of a steel sheet with a thickness of 0.05 to 0.5 mm, and the micropore area of the steel sheet contains 1500-10000 micropores with diameters ranging from 2 to 5 microns.

8. The high-frequency ultrasonic atomizer structure of claim 1, wherein the main machine comprises:

a housing with keys arranged on a surface thereof, a battery arranged in the housing, a circuit board arranged at a position corresponding to where the keys are arranged on the housing and connected to the battery, a second connecting tube arranged at an end of the housing, having internal threads and correspondingly connected with external threads on the first connecting tube, and a second electrode arranged in the second connecting tube and connected to the battery, wherein, the first electrode is connected to the second electrode.

9. The high-frequency ultrasonic atomizer structure of claim 8, wherein the circuit board comprises:

a main control unit, an atomization piece driving unit connected to the main control unit, a key unit that are respectively connected to the main control unit, a boosting unit connected to the atomization piece driving unit, and a second motor connected to the atomization piece driving unit, wherein, the boosting unit is connected to the battery.

10. The high-frequency ultrasonic atomizer structure of claim 9, wherein the atomization piece driving unit is electrically powered through the second electrode, the first electrode and the piezoelectric ceramic piece in sequence.

* * * * *